United States Patent [19]
Morejon

[11] Patent Number: 6,082,361
[45] Date of Patent: *Jul. 4, 2000

[54] ENDOTRACHEAL TUBE CLEANING APPARATUS

[76] Inventor: Orlando Morejon, 235 SW. 79th Ave., Miami, Fla. 33144

[ * ] Notice: This patent is subject to a terminal disclaimer.

[21] Appl. No.: 08/928,113

[22] Filed: Sep. 12, 1997

[51] Int. Cl.$^7$ .................................................. A61M 16/00
[52] U.S. Cl. .............................. 128/207.15; 128/207.14; 128/912
[58] Field of Search ......................... 128/207.15, 207.14, 128/200.26, 911, 912, 202.27, 207.18; 604/280, 264; 600/572; 606/106, 196

[56] References Cited

U.S. PATENT DOCUMENTS

| | | |
|---|---|---|
| 2,910,981 | 11/1959 | Wilson et al. . |
| 3,991,762 | 11/1976 | Radford . |
| 4,327,723 | 5/1982 | Frankhouser . |
| 4,515,592 | 5/1985 | Frankhouser . |
| 4,569,344 | 2/1986 | Palmer . |
| 4,638,539 | 1/1987 | Palmer . |
| 4,696,296 | 9/1987 | Palmer . |
| 4,762,125 | 8/1988 | Leiman et al. ..................... 128/207.15 |
| 4,825,859 | 5/1989 | Lambert .............................. 128/202.16 |
| 4,836,199 | 6/1989 | Palmer . |
| 4,872,579 | 10/1989 | Palmer . |
| 4,938,741 | 7/1990 | Lambert . |
| 5,003,657 | 4/1991 | Boiteau et al. .......................... 604/158 |
| 5,269,759 | 12/1993 | Doyden .................................... 128/912 |
| 5,542,938 | 8/1996 | Avellanet et al. ...................... 604/280 |
| 5,642,726 | 7/1997 | Owens et al. ....................... 128/200.26 |
| 5,709,691 | 1/1998 | Morejon ............................. 128/207.14 |
| 5,711,294 | 1/1998 | Kee et al. ........................... 128/202.27 |

Primary Examiner—John G. Weiss
Assistant Examiner—V. Srivastava
Attorney, Agent, or Firm—Malloy & Malloy, P.A.

[57] ABSTRACT

An endotracheal tube cleaning apparatus to be used with an endotracheal tube, the cleaning apparatus having an elongate tubular member with a distal end that extends into the endotracheal tube and at least one channel defined therethrough and terminating at a distal end disposed in a vicinity of the distal end of the elongate tubular member. A cleaning assembly is provided at the distal end of the elongate tubular member so as to affirmatively engage the interior wall structure of the endotracheal tube, as a result of a resilient material bladder, for cleaning thereof. A ventilator coupling is further provided and is connected to the endotracheal tube. Moreover, a first inlet port of the ventilator coupling is coupled to a ventilator assembly structured to supply air to a patient, and a second inlet port of the ventilator coupling is structured to receive the elongate tubular member therethrough into the endotracheal tube. Also, a bypass coupling assembly is provided and connected in fluid flow communication between the channel of the elongate tubular member and the ventilator assembly so as to automatically direct air from the ventilator assembly into the channel of the elongate tubular member, and out the distal end of the channel, upon occlusion of a flow of the air through the endotracheal tube at a point of the endotracheal tube upstream of the distal end of the channel.

39 Claims, 6 Drawing Sheets

ENDOTRACHEAL TUBE CLEANING APPARATUS

BACKGROUND OF THE INVENTION

1. Field of the Invention

The present invention relates to an endotracheal tube cleaning apparatus to be used to effectively and efficiently clean the flow through passage of an endotracheal tube, including the effective removal of even solid buildup on the interior wall surface of the endotracheal tube safely, effectively, and in a self contained sterile assembly that does not have to be removed from the patient and does not significantly restrict airflow to the patient. Furthermore, the cleaning apparatus is structured to ensure that a patient is still capable of effective breathing, even during cleaning, and to enable effective examination and cleaning of the cleaning assembly during continued uses, thereby ensuring that excessive build up is not on the cleaning assembly during continued cleaning of the endotracheal tube.

2. Description of the Related Art

Many patients in a hospital, and in particular, patients in an Intensive Care Unit ("ICU") must be fitted with endotracheal tubes to facilitate their respiration. Specifically, an endotracheal tube is an elongate, semi-rigid lumen which is inserted into a patient's nose or throat and projects down into airflow communication with the patient's respiratory system. As such, the patient either directly, or with the aid of a respiratory unit, is able to breathe more effectively through the endotracheal tube.

Recent studies have determined, however, that the accumulation of dried tracheobronchial secretions on the interior wall surface of an operating endotracheal tube effectively decreases the lumen cross section, and thereby significantly increases the work of breathing for the intubated patient. Moreover, increasing the work of breathing for the patient necessitates that a higher level of support be provided to compensate, and often results in the patient's intubation period and ICU stay being significantly prolonged. Furthermore, it is also seen that thick secretions on the walls of the endotracheal tube often serve as a nidus for continued infection in the lungs, leading to added morbidity and hospital costs for the intubated patient.

To date, the only effective means of eliminating the accumulated secretions within an endotracheal tube completely, has been to exchange the contaminated endotracheal tube for a new tube. There are, however, several disadvantages to this procedure, such as temporary arrest of ventilatory support and the risk of complete loss of airway control. For example, re-intubation may be exceedingly difficult in patients with swelling of the soft tissue of the neck, and in patients having cervical spine immobilization, because upon removal of the endotracheal tube, the appropriate internal passages tend to close up and be otherwise difficult to isolate for reintroduction of a new endotracheal tube. Further, re-intubation of a patient can result in additional trauma to the oral, laryngeal and tracheal tissues.

Short of replacing the endotracheal tube completely, the only other means currently in use for maintaining endotracheal tubes somewhat clear is the use of flexible suction/irrigation catheters. Specifically, these suction/irrigation catheters, are passed down the endotracheal tube and upper airways and seek to evacuate contaminants from the lumen. Unfortunately, although the suction/irrigation catheters generally clear the airway of watery secretions, they are ineffective at clearing the inspissated secretions that have accumulated on the inner wall surface of the endotracheal tube over the course of days. In essence, the use of a suction/irrigation catheter merely delays the inevitable, namely, that the endotracheal tube be removed and replaced.

One somewhat recent attempt to address the problems associated with the maintenance of endotracheal tubes is seen to provide a two part assembly which is introduced into the flow through passage of the endotracheal tube. Specifically, a thin interior, solid segment having a plurality of retracting bristles and a sealing gasket at an end thereof is contained within an exterior lumen. In use, the entire coupled assembly is introduced into the endotracheal tube, but the interior segment is pushed through the outer tube so that the bristles expand to engage the wall surface, and the gasket member, such as a foam cylinder or balloon, expands to completely seal off the area behind the bristles. The entire device, including the upwardly angled bristles is then pulled upwardly with the gasket element completely sealing off the tube there below so that any debris removed by the bristles is retained. Such a device, however, does not provide for accurate insertion indication to prevent over-insertion into the endotracheal tube, and completely seals off the endotracheal tube during removal so as to result in a potentially hazardous interruption to ventilation and/or a negative pressure or suction behind the cleansing device. Furthermore, it is seen from the need to include the bristles, that direct engagement of a gasket type member, such as the balloon, with the interior wall surface of the endotracheal tube, does not provide for the complete and effective removal of secretions, due primarily to the smooth exterior surface of the gasket. Moreover, the smooth resilient material surface also results in substantial friction between the rubbery gasket and the plastic wall surface, thereby making it quite difficult to smoothly and effectively pull the cleansing device from the endotracheal tube. Additionally, it is seen that upwardly angled bristle members are susceptible to complete or partial retraction as they encounter obstacles and attempt to scrape clean the interior of the endotracheal tube, and in fact, the bristle members are often quite sharp and may be damaging to the endotracheal tube or to a patient if inadvertently projected beyond the endotracheal tube so that the outwardly projecting bristle members become stuck outside the endotracheal tube. Also, because of the collapsing configuration of bristles, gaps will naturally exist between adjacent bristles and some areas of the tube are not engaged, and as secretions begin to build up beneath the bristles, their collapse is further restricted. Further, such a single function device necessitates that additional items be introduced into the tube, generally resulting in additional trauma to the patient, if some suction is necessary.

As such, there is still a substantial need in the art for a cleaning device that can be used to clear endotracheal tube secretions effectively, and on a regular basis, thereby expediting ventilatory weaning and extubation of ICU patients. Further, there is a need for an effective endotracheal tube cleaning apparatus which can be easily and effectively introduced into the endotracheal tube, and which can be easily removed, even though it effectively removes solid secretion buildup, due to its friction minimizing engagement with the interior wall surface of the endotracheal tube and/or because of its alleviation of negative pressure/suction within the endotracheal tube upon removal thereof. Additionally, there is a need for a cleaning device which can be accurately extended into the endotracheal tube without substantial risk of over introduction, will not become lodged through the endotracheal tube in the event that it protrudes slightly from the end of the endotracheal tube, and which can be utilized for multiple functions, such as the introduction of medication deep into the patient's airway.

In addition to the referenced needs in the industry, it is also noted that an effective cleaning device should preferably be configured to maintain air flow/ventilation to a patient during substantially all phases of cleaning. Moreover, the device should maintain maximum sterile integrity as to those components which will be ultimately introduced into the patient, providing for effective cleaning and/or monitoring thereof.

SUMMARY OF THE INVENTION

The present invention is directed towards an endotracheal tube cleaning apparatus to be used to clean an endotracheal tube while it is being used in an intubated patient. Typically, the endotracheal tube is of the type that includes a central lumen, defined by an interior wall structure that extends from a distal end to a proximal end of the tube.

Specifically, the endotracheal tube cleaning apparatus includes an elongate tubular member having a diameter smaller than the interior diameter of the endotracheal tube. Further, the elongate tubular member includes a distal end that is structured to be introduced and extend into the lumen of the endotracheal tube. Defined within the elongate tubular member, and extending from generally its first/proximal end to its second/distal end is a channel. The channel provides a fluid flow through conduit that terminates in an outlet port defined in the elongate tubular member, generally near the second end thereof.

Also disposed in a vicinity of the distal end of the elongate tubular member is a cleaning assembly. The cleaning assembly, which includes an inflatable resilient material bladder having an exterior abrasive surface, is structured to affirmatively engage the interior wall structure of the endotracheal tube with some outward cleaning pressure, for subsequent cleaning of the endotracheal tube upon reciprocating movement of the elongate tubular member within the endotracheal tube.

Additionally, the endotracheal tube cleaning apparatus includes a ventilator coupling. The ventilator coupling is structured to be coupled in fluid flow communication with the endotracheal tube, and includes a first inlet port and a second inlet port defined therein. Specifically, the first inlet port is structured to be coupled to a ventilator assembly and thereby provide air to the patient in a conventional manner through the endotracheal tube. The second inlet port, however, is structured to receive the elongate tubular member therethrough for subsequent passage into the endotracheal tube, and as such is preferably disposed in axial alignment with the endotracheal tube.

In order to ensure that the patient is consistently ventilated, a bypass coupling assembly is further provided. The bypass coupling assembly is disposed/connected in fluid flow communication between the channel of the elongate tubular member and the ventilator assembly. Moreover, it is structured and disposed to automatically direct the fluid from the ventilator assembly, into the channel of the elongate tubular member, and out the distal end of the channel, upon occlusion of a flow of air through the endotracheal tube at a point of the endotracheal tube upstream of the distal end of the channel. Accordingly, if normal ventilation stops, ventilation through the bypass coupling assembly will continue.

It is an object of the present invention to provide an endotracheal tube cleaning apparatus which can efficiently and easily be routinely utilized to maintain the flow through passage of an endotracheal tube free from the accumulation of dried tracheobronchial secretions.

A further object of the present invention is to provide an endotracheal tube cleaning apparatus which can easily and effectively be oriented so as to prevent over insertion into endotracheal tubes of varying lengths.

Yet another object of the present invention is to provide an endotracheal tube cleaning apparatus which can absorb watery secretions as well as remove dried secretions from the interior wall surface of an endotracheal tube.

Also an object of the present invention is to provide an endotracheal tube cleaning apparatus which provides sufficient abrasion to remove dried secretions from the interior wall surface, but which is also substantially smooth and easy to slidingly remove from the endotracheal tube while it is engaged with the interior wall surface thereof.

Another object of the present invention is to provide an endotracheal tube cleaning apparatus which can provide effective cleaning pressure on the interior wall surface of the endotracheal tube, but which provides minimal risk of external contamination through the rupture of a resilient material bladder thereof.

A further object of the present invention is to provide an endotracheal tube cleaning apparatus which can alleviate negative pressure deep within the endotracheal tube while the cleaning device is engaging the wall surface of the endotracheal tube during cleaning.

Still another object of the present invention is to provide an endotracheal tube cleaning apparatus which can simultaneously provide abrasive dried secretion removal with effective suction/irrigation to remove watery secretions.

Yet another object of the present invention is to provide an endotracheal tube cleaning apparatus which can be utilized to perform a variety of functions during a single insertion.

Another object of the present invention is to provide an endotracheal tube cleaning apparatus which can be utilized to suction a patient's airway and will not harm the patient if inserted beyond the tube for that purpose.

Also an object of the present invention is to provide an endotracheal tube cleaning apparatus which automatically functions to ensure that a patient is ventilated, even if normal air flow through the endotracheal tube is occluded during cleaning.

A further object of the present invention is to provide an endotracheal tube cleaning apparatus which can provide for effective, isolated irrigation of the cleaning assembly, thereby permitting safe re-introduction and added cleaning of the endotracheal tube therewith.

Also an object of the present invention is to provide an endotracheal tube cleaning apparatus which can assist with the introduction of medication at an effective deployment site within the patient's airway.

Another object of the present invention is to provide an endotracheal tube cleaning apparatus which is convenient to grasp and manipulate and which provides for easy adjustment of the inflated amount of the resilient material bladder.

An added advantage of the present invention is to provide an endotracheal tube cleaning apparatus which is substantially sterile and contained both during introduction and during removal and internal irrigation.

A further object of the present invention is to provide a cap assembly which remains in a substantially protected state both when in use and not in use.

BRIEF DESCRIPTIONS OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE PREFERRED EMBODIMENT

Figure 1:
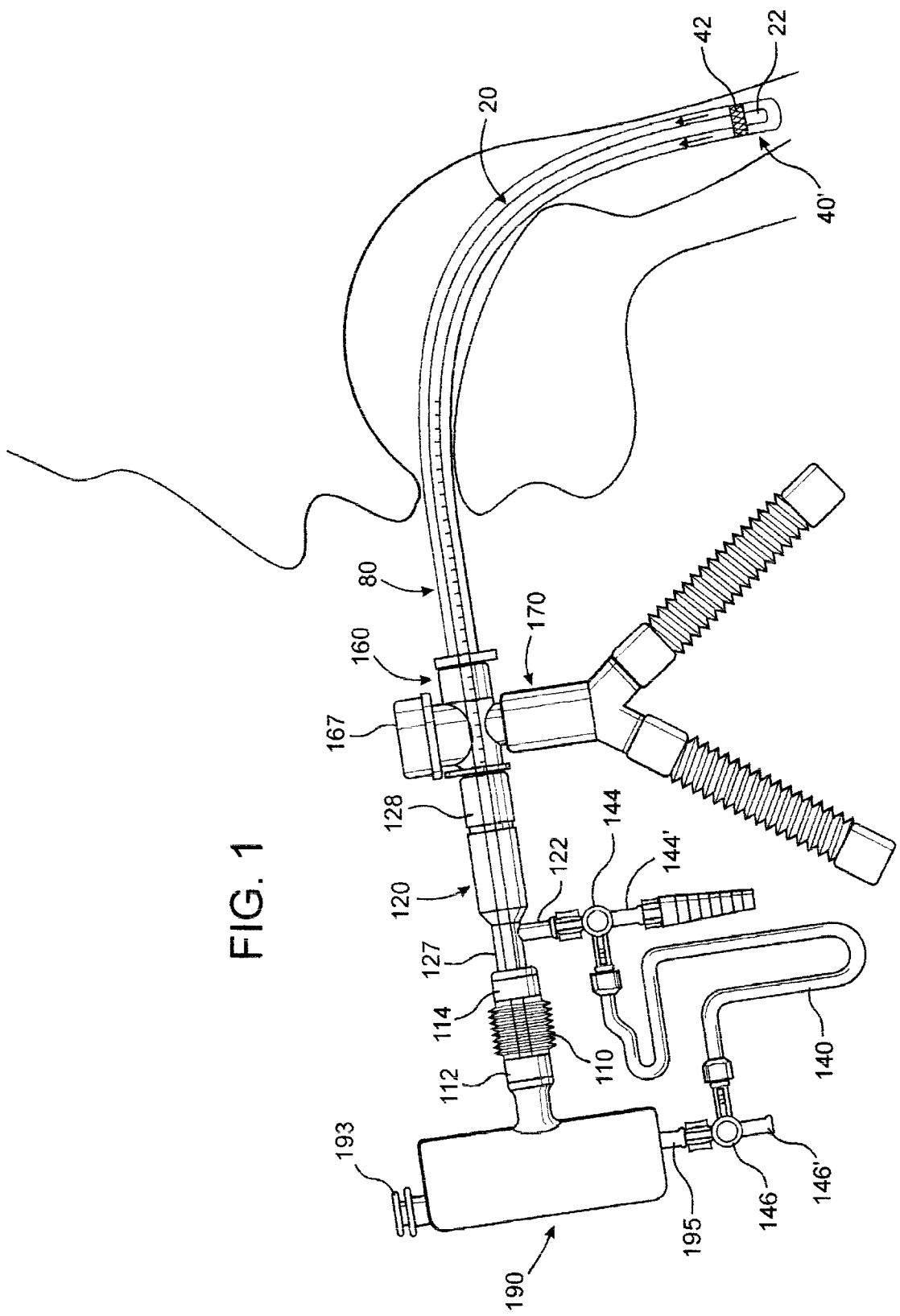
FIG. 1 is a side view of the endotracheal tube cleaning apparatus of the present invention in an operative orientation within an endotracheal tube.
Figure 2:
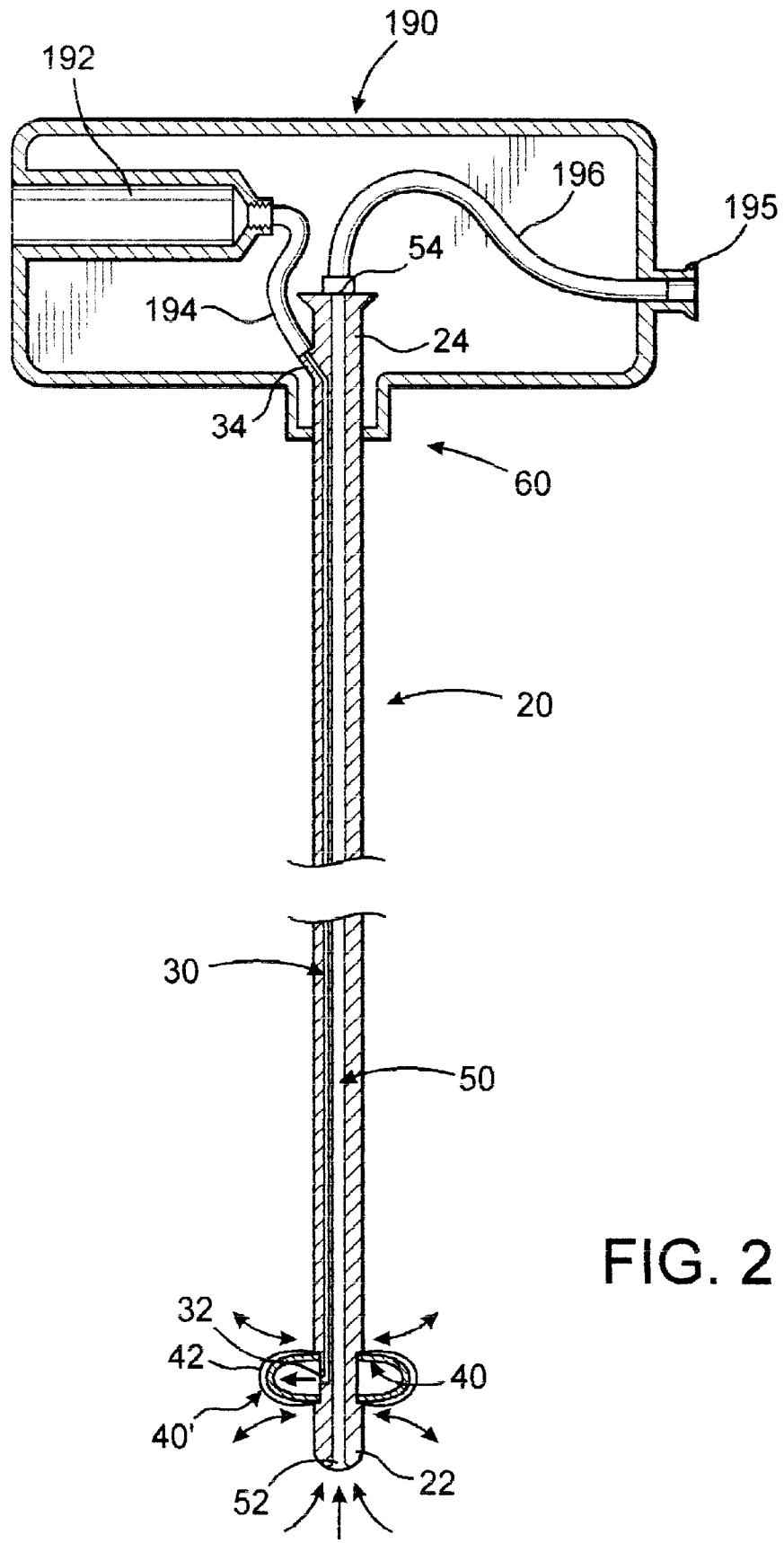
FIG. 2 is an isolated, side cross-sectional view of the elongate tubular member and handle assembly of the endotracheal tube cleaning apparatus of the present invention.
Figure 3:
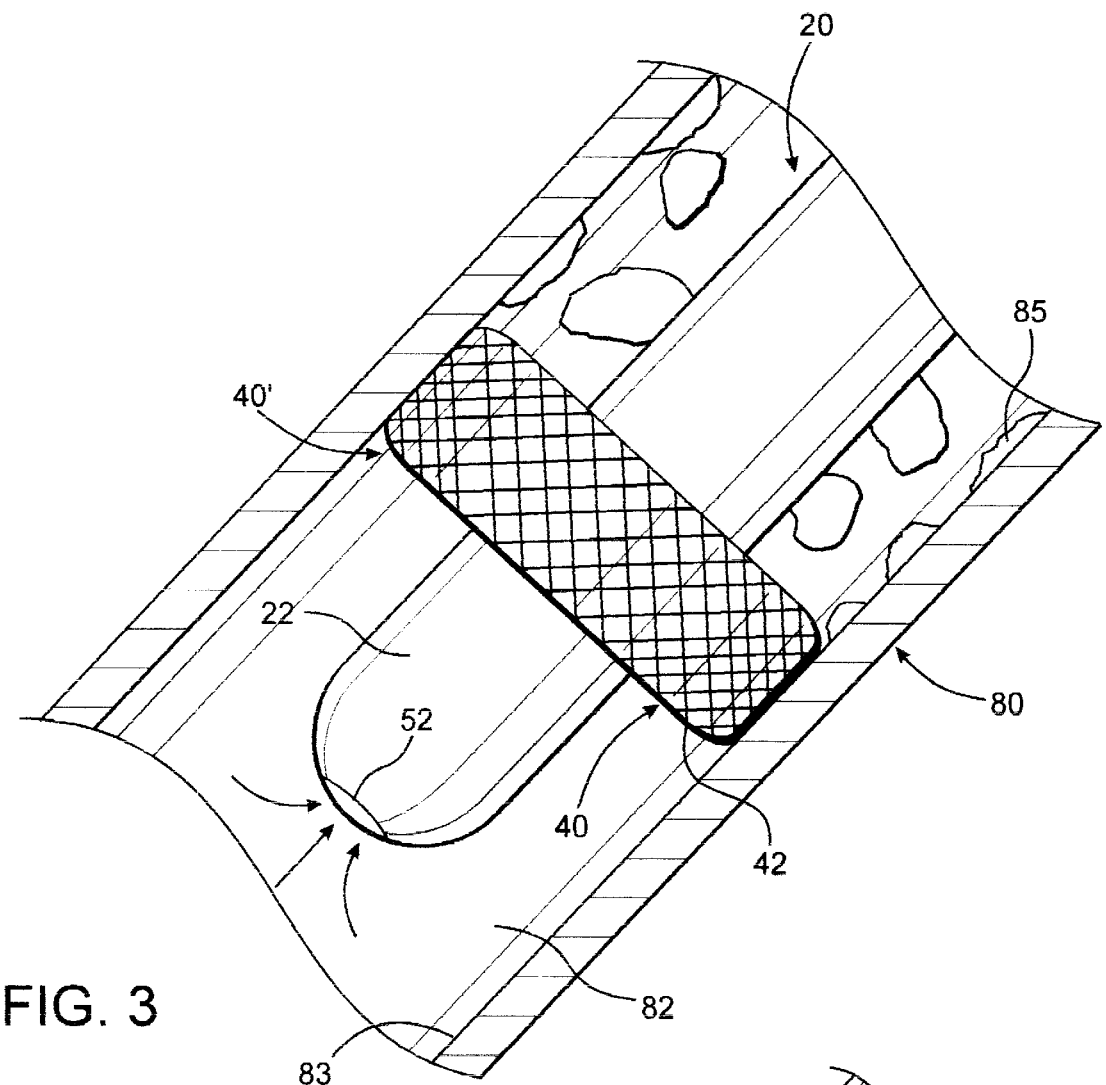
FIG. 3 is an isolated side view of the resilient material bladder and exterior sheath in an operative, cleaning position within an endotracheal tube.

Shown throughout the Figures, the present invention is directed toward an endotracheal tube cleaning apparatus, generally indicated as 10. In particular, the endotracheal tube cleaning apparatus 10 is constructed for use with an endotracheal tube 80 that is conventionally utilized to enable a patient to breathe, and as such, is generally inserted down the throat of a patient as illustrated in FIG. 1. Such an endotracheal tube 80 is preferably of the type including a flow through passage 82 having an interior wall surface 83 that defines its interior diameter. Generally, however, after prolonged periods of use, the endotracheal tube 80 will exhibit a buildup of secretions 85 that form on the interior wall surface 83 and can thereby obstruct airflow through the flow through passage 82. The endotracheal tube cleaning apparatus 10 of the present invention, among other functions, is structured to facilitate the removal of those secretions 85 in a convenient and effective manner.

In particular, the endotracheal tube cleaning apparatus 10 of the present includes an elongate tubular member 20 having a first/proximal end 24 and a second/distal end 22. The elongate tubular member 20, which is preferably of a semirigid construction so as to allow it to bend and conform to the operative configuration of the endotracheal tube 80 within a patient, has a length at least equivalent to a length of the endotracheal tube 80. As such, the endotracheal tube cleaning apparatus 10 can effectively reach deep down into the length of the endotracheal tube 80 for effective cleaning of even the most remotely introduced portions thereof. Furthermore, the elongate tubular member 20 is structured with a diameter smaller than the interior diameter of the endotracheal tube 80, and in fact, is preferably quite narrow so as to facilitate the introduction of the elongate tubular member 20 into endotracheal tubes of varying sizes and permit normal airflow thereabout in most circumstances. Preferably disposed on an exterior surface of the elongate tubular member 20 is a gradiated indicia 62. In particular, it is generally not favorable for the second end 22 of the elongate tubular member 20 to penetrate beyond an open end of the endotracheal tube 80, as it may come in contact with interior organs and/or tissue of the patient. As such, upon knowing the dimensions of the endotracheal tube 80 being utilized within the patient, a user can make note of an appropriate marking on the indicia 62, which may include lines or preferably numerals, to ensure that the elongate tubular member 20 is not over inserted into the endotracheal tube 80.

Preferably defined within the elongate tubular member 20 is an inflation channel 30. Specifically, the inflation channel 30 is structured to extend from generally the first end 24 of the elongate tubular member 20 towards the second end 22 of the elongate tubular member 20. Moreover, the inflation channel 30 will preferably terminate in an outlet port 32 defined generally near the second end 22 of the elongate tubular member 20. The outlet port 32 of the inflation channel 30 is structured and disposed so as to permit the escape of a fluid, such as air, therethrough, subsequent to its passage through the length of elongate tubular member 20 within the inflation channel 30. As illustrated in the preferred embodiment of the drawings, the outlet port 32 of the inflation channel 30 preferably extends out a side of the elongate tubular member 20, in a vicinity of the second end 22 of the elongate tubular member 20, and may preferably extend into an annular track defined in the elongate tubular member 20.

Secured to the elongate tubular member 20, also generally at the second end 22 thereof as part of a cleaning assembly 40' is a resilient material bladder 40. Preferably the resilient material bladder 40 engages the elongate tubular member 20 within the annular track, and as such is disposed over the outlet port 32 of the inflation channel 30. Accordingly, the resilient material bladder 40 is structured and disposed to be in fluid flow communication with the outlet port 32 and hence the inflation channel 30. Therefore, when a fluid, such as air, exits the inflation channel 30 through the outlet port 32, it will pass into the resilient material bladder 40 to result in a corresponding inflation thereof. Specifically, the resilient material bladder 40 is formed of an expandable material and is preferably structured to inflate to at least a diameter that is approximately equivalent to a diameter of the interior wall surface 83 of the endotracheal tube 80, thereby exerting some outward pressure on the endotracheal tube 80 when it is inflated. Additionally, the resilient material bladder 40 may be sized to be variably inflated and thereby permit effective use of the endotracheal tube cleaning apparatus 10 within endotracheal tubes 80 having varying interior diameters. The resilient material bladder 40 may be secured to the elongate tubular member 20 in a variety of fashions, and may take on a variety of configurations effective to provide for appropriate inflation and secure retention at generally the second end 22 of the elongate tubular member 20. By way of example, the resilient material bladder 40 can have an inner-tube type configuration secured to the elongate tubular member 20 and having inlet opening connected in fluid flow communication with the outlet port 32 of the inflation channel 30. Alternatively, the resilient material bladder 40 can have a tire-type configuration wherein the resilient material 40 has a generally C-shaped cross section and forms a seal between its edges and the exterior surface of the elongate tubular member 20 in order to captivate air therebetween for the resultant inflation of the resilient material bladder 40.

Figure 4:
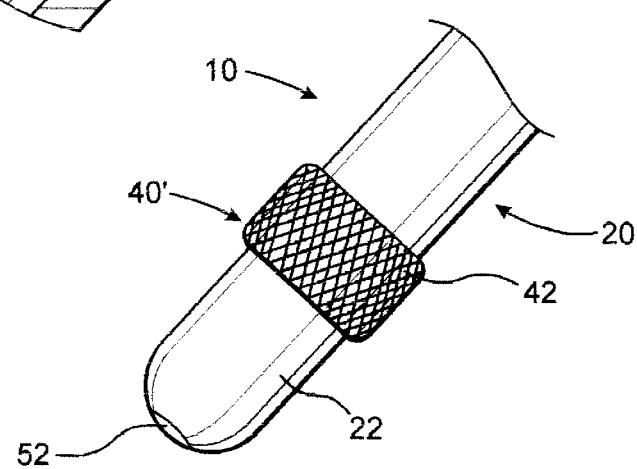
FIG. 4 is an isolated view of the elongate tubular member of the endotracheal tube cleaning apparatus of the present invention illustrating the orientation of the resilient material bladder and expandable exterior sheath when not in an operable, cleaning orientation.
Figure 5:
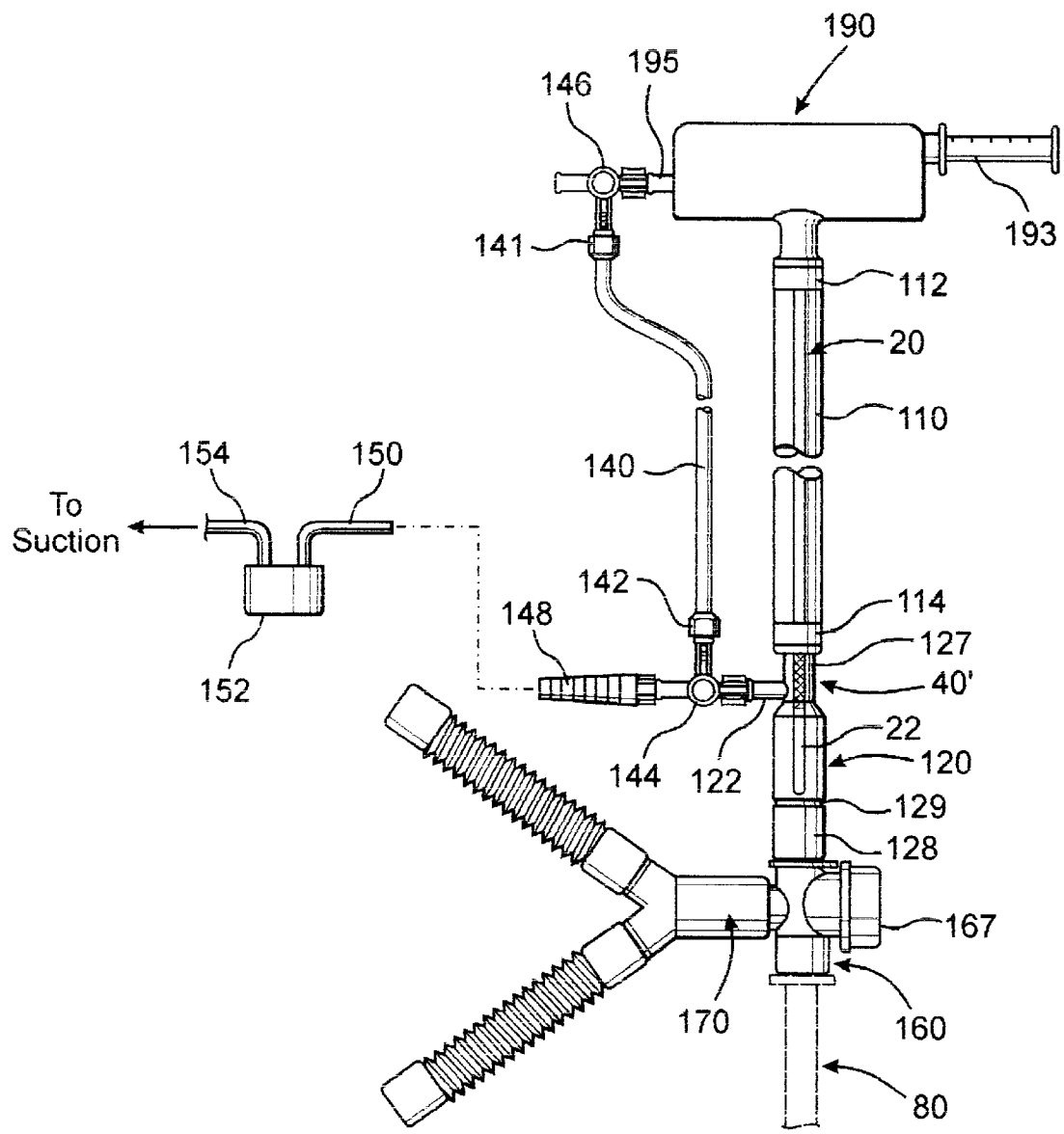
FIG. 5 is an isolate view of the preferred embodiment of the endotracheal tube cleaning apparatus of the present invention.
Figure 6:
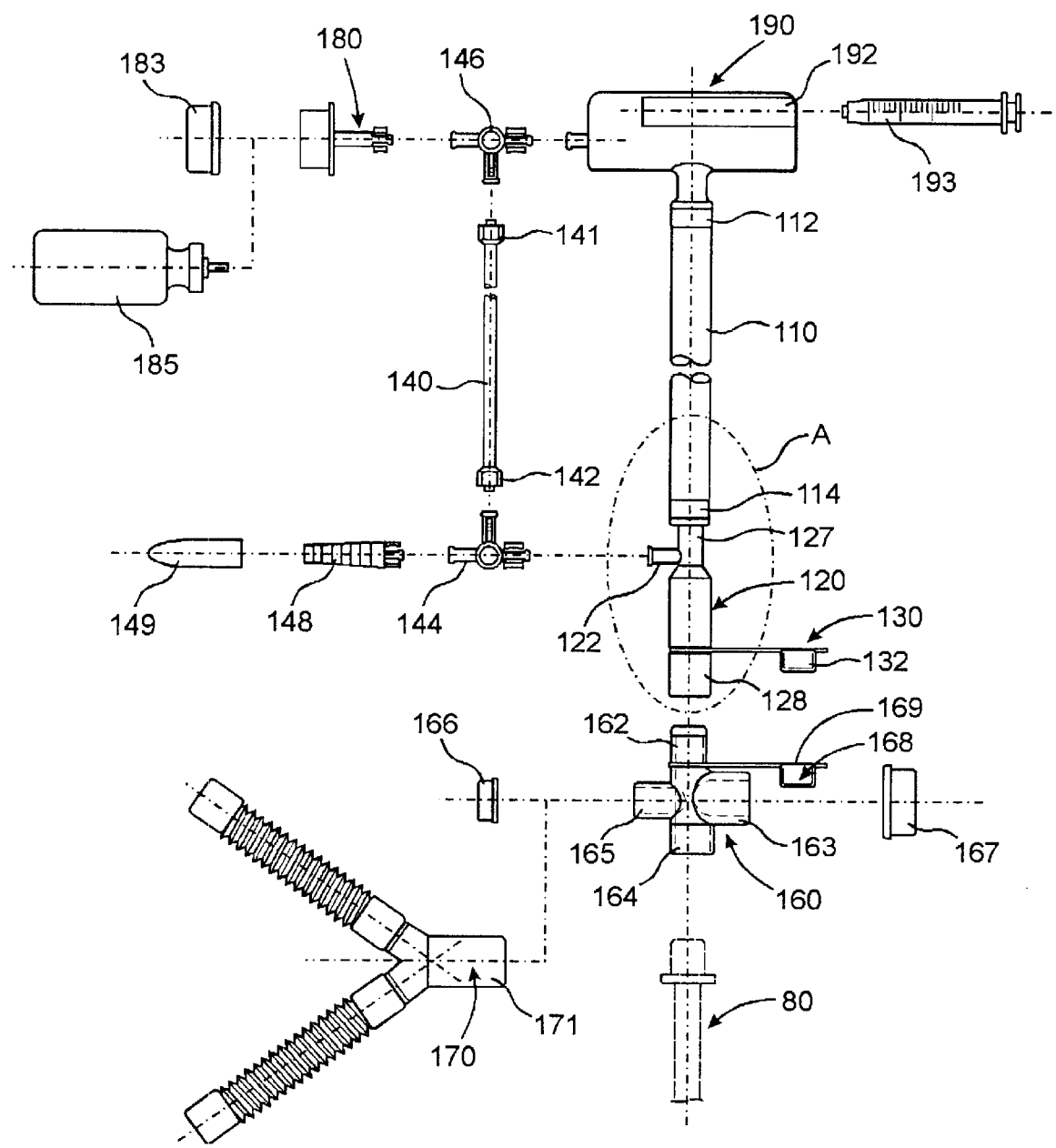
FIG. 6 is an exploded view of the preferred embodiment of the endotracheal tube cleaning apparatus of the present invention.
Figure 7:
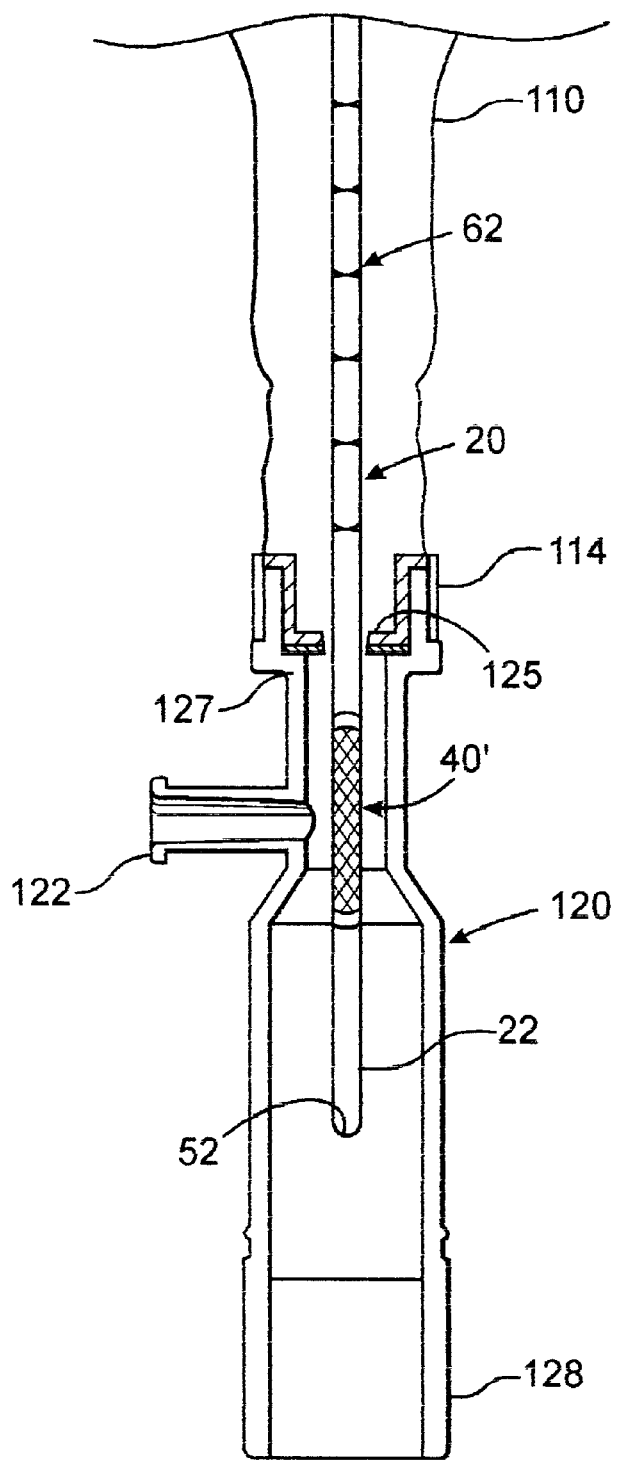
FIG. 7 is an isolated, enlarged, cross section view of area A of FIG. 6.

Disposed at least partially, but preferably completely about the resilient material bladder 40 is an expandable, exterior sheath 42. In the preferred embodiment, the expandable exterior sheath 42 is specifically structured and disposed to completely contain the resilient material bladder 40, and thereby prevent passage of any portion of the resilient material bladder 40 down into the endotracheal tube 80 should the resilient material bladder 40 rupture during inflated use. Furthermore, the expandable, exterior sheath includes an exterior, generally abrasive surface, preferably along an entire exterior surface of the exterior sheath, which will engage, with a degree of outward cleaning pressure as translated from the resilient material bladder to which it conforms, and will thereby clean the entire interior wall surface 83 of the endotracheal tube 80 when the resilient material panel 40 is inflated. Preferably, the expandable exterior sheath 40 has a soft, expandable, mesh type configuration which can engage an entire circumference of the interior wall surface 83 with a generally large surface area. Conversely, when the resilient material bladder 40 is collapsed, as illustrated in FIG. 4, the expandable exterior sheath 42 is also collapsed, but does not sag or droop. Rather, the gaps within the mesh type configuration of the expandable exterior sheath 42 will merely reduce and the mesh will normally maintain its more tightly packed mesh configuration. Alternatively, however, when the resilient material bladder 40 is inflated, the expandable mesh type configuration of the expandable exterior sheath 42 permits it to stretch out and maintain its covering relation over the resilient material bladder 40. It is therefore seen, that the plurality of openings defined in the expandable exterior sheath 42, when it is expanded and wrapped about an inflated, operable resilient material bladder 40, provide a generally abrasive exterior surface that when passed over the interior wall surface 83 of the endotracheal tube 80 with some outward cleaning pressure, will function to loosen the secretions 85 that are stuck to the interior wall surface 83 of the endotracheal tube 80. Accordingly, effective cleaning results when the resilient material bladder 40 is inflated and the elongate tubular member 20 is pulled out from its inserted orientation within the flow through passage 82 of the endotracheal tube. It is also seen, however, that some in and out, reciprocating movement of the elongate tubular member 20 may be necessary to provide for complete and effective secretion 85 removal. Moreover, in the preferred embodiment, a small distance, namely a safety distance, is preferably maintained between the resilient material bladder 40 and the tip of the elongate tubular member 20 at the second end 22. Accordingly, a risk of over introduction of the cleaning assembly 40' beyond the endotracheal tube 80 is minimized when an introduction distance is equated to a length of the elongate tubular member 20, as will be described.

In addition to containing the resilient material bladder 40 in case of rupture, and providing the exterior, generally abrasive surface necessary for cleaning, the expandable exterior sheath 42, which may be formed of a nylon or other soft material mesh, also provides a smooth exterior surface that facilitates movement during introduction and removal of the resilient material bladder 40, and therefore the elongate tubular member 20, into and out of the endotracheal tube 80 during cleaning. Specifically, because of the material construction of the resilient material bladder 40, significant friction may be exhibited between the resilient bladder 40 itself, and the interior wall surface 83 of the endotracheal tube 80. Such frictional resistance may make it quite difficult, or at least quite erratic during the removal and/or reintroduction of the resilient material bladder 40 into the endotracheal tube 80. Furthermore, the expandable exterior sheath can more effectively absorb and/or remove the secretions if the resilient material bladder 40 can be retained in an inflated orientation as the endotracheal tube cleaning apparatus 10 is completely removed from the endotracheal tube 80, because any dislodged secretions 85 are substantially prevented from dropping beneath the resilient material bladder 40 where they may fall into the patient.

Disposed opposite the outlet port 32 of the inflation channel 30, and also connected in fluid flow communication with the inflation channel 30 is an inlet port 34. Specifically, the inlet port 34 is structured to permit the introduction of a fluid, preferably air, into the inflation channel 30 for subsequent inflation of the resilient material bladder 40. While this inlet port 34 may be positioned anywhere in the elongate tubular member 20, it is preferred that it be positioned generally near the first end 24 thereof in order to permit the facilitated introduction of fluid therethrough when the elongate tubular member 20 is substantially introduced into the endotracheal tube 80. Moreover, in a preferred embodiment the inlet port 34 is operatively disposed at a slight angle from an axis of the elongate tubular member 20 to permit facilitated introduction of air into the channel 30.

Looking to the preferred embodiment of the figures, coupled to the elongate tubular member 20, preferably at its first end 24, is a handle assembly 190. Specifically, the handle assembly 190 is preferably disposed in a generally perpendicular orientation relative to the elongate tubular member 20, and may include a generally T-shaped configuration. As such, it is seen that a user may grasp the handle assembly 190 with the elongate tubular member 20 extending out from between the user's fingers, and reciprocating movement of the elongate tubular member 20 within the endotracheal tube 80 is greatly facilitated.

Preferably included within the handle assembly 190 is an inflation assembly. In particular, the inflation assembly is structured to facilitate the introduction of the fluid into the inflation channel 30 of the elongate tubular member 20 through the inlet port 34. In the preferred embodiment, the inflation assembly includes a chamber 192 defined therein and disposed in fluid flow communication via a conduit 194 with the inlet port 34. As such, it is seen that the handle assembly 190 preferably encases the first end 24 of the elongate tubular member 20 such that the interconnection with the inlet port 34 is internally contained. Of course a number of coupled interconnections can be achieved between the conduit 194 and the inlet port 34 and chamber 192, such as threaded, snap-fit, friction, or molded connections. Moreover, the conduit 194 may include a separate flexible element or may be molded directly into the body of the handle assembly 190. Looking to the chamber 192, although a variety of separate and/or integrally molded inflation mechanisms may be provided for connection at the chamber 192, it is preferably structured to receive a hypodermic syringe 193 therein. The syringe 193, which typically includes a threaded hub tip, is structured to screw into, or be otherwise coupled within the chamber 192 so as to direct air or liquid exiting the syringe 193 into the conduit 194. Accordingly, with the perpendicular configuration of the handle assembly 190, it is seen that a user grasping the handle assembly 190 may also easily place his/her thumb in actuating relation on the syringe 193. Therefore, a user can actually control the amount of fluid 16 within the inflatable bladder 40, and the outward pressure being exerted thereby on the endotracheal tube 80, while reciprocating movement of the elongate tubular member 20 is performed. Also, although separate valve means may be provided to restrict the escape of fluid after the resilient material bladder has been filled, in circumstances were the syringe 193 is coupled to the handle assembly 190 and therefore the channel 30 at the inlet port 34, it functions to prevent the escape of air and the deflation of the resilient material bladder 40 while pressure is maintained thereon by the user.

Also in the preferred embodiment, the endotracheal tube cleaning apparatus 10 of the present invention includes an equilibrium channel 50. Specifically, the equilibrium channel 50 includes a distal end and a proximal end and is defined in the elongate tubular member 20 so as to extend from generally the first end 24 of the elongate tubular member 20 to generally the second end 22 of the elongate tubular member 20, at a point beyond the resilient material bladder 40. Moreover, the equilibrium channel 50 includes ports 52 and 54 at generally the first and second ends of the elongate tubular member 20. Accordingly, the equilibrium channel 50 will provide a passage that significantly alleviates suction/negative pressure behind the resilient material bladder 40 as it is being removed from the endotracheal tube 80 in its inflated orientation. It is understood, that when the resilient material bladder 40 is inflated it effectively forms a seal with the interior wall surface 83 of the endotracheal tube 80. Therefore, as the elongate tubular member 20 is pulled for cleaning, a suction effect behind the resilient material 40 can result. Not only can this suction effect make it substantially more difficult to remove the endotracheal tube cleaning apparatus 10 from the endotracheal tube 80, but some trauma can result to the patient as a result of this suction effect and a loss of continued ventilation through the endotracheal 80 can result. Through the positioning of the equilibrium channel 50, the suction pressure is alleviated, and in fact, some air flow may be provided to the patient therethrough. Moreover, as will be described subsequently, the equilibrium channel 50 can be used as a conduit for various other functions of the present invention.

While the elongate tubular member 20 may be structured so as to be extended directly through a conventional Y-connector of the ventilator assembly 170 implemented in a normal fashion at an exposed end of the endotracheal tube 80, thereby permitting the continuance of air flow through one inlet of the Y-connector, while permitting introduction of the elongate tubular member 20 through the other inlet of the Y-connector, in the preferred embodiment, a ventilator coupling 160 is provided. Specifically, the ventilator coupling 160 includes at least two, but preferably three inlet ports 162, 163 & 165, and an outlet port 164. The outlet port 164 is structured to be coupled, preferably directly with the endotracheal tube 80, in a standard manner so as to allow complete access to the endotracheal tube 80 therethrough. Similarly, the first inlet port 165 is structured to be coupled directly to the ventilator assembly 170 at a connector hub 171 thereof. A typical press fit engagement may also be provided. Along these lines, however, and because ventilators having varying sized connector hubs 171 may be provided, the preferred third inlet port 163 is also provided and configured of an alternative diameter to be coupled to a ventilator assembly. For example, one inlet port may be 22 mm and another 15 mm. Of course, when a particular inlet port 163 or 165 is not in use for connection with the ventilator assembly 170, it may be used to provide access for other purposes and to other implements, or it may be merely sealed of by a corresponding cap 166 or 167. Looking to the second inlet port 162, it is structured to receive the elongate tubular member 20 therethrough, and is therefor preferably disposed directly in axial alignment with the entrance of the endotracheal tube 80.

In the preferred embodiment, the second inlet port 162 is coupled with a hub assembly 120 at an open second end 128 thereof. Specifically, the hub assembly 120 is structured to receive and preferably guide the elongate tubular member 20 therethrough and into the endotracheal tube 80 through the ventilator coupling 160. Moreover, when retracted, the second end 22 of the elongate tubular member 20 is preferably disposed in the hub assembly 120 to provide some sanitary containment.

Extending from a first end 127 of the hub assembly 120 is a collapsible exterior sheath 110. Specifically, the exterior sheath 110 is formed of a flexible, preferably transparent material, and is secured at opposite ends thereof between the handle assembly 190 and the hub assembly 120. A typical collar coupling 112 and 114 is preferred so as to prevent separation. As such, a length of the exterior sheath 110 functions to restrict outward removal of the elongate tubular member 20 completely out of the hub assembly 120. Moreover, the elongate tubular member 20 is maintained in a completely isolated, completely sterile environment to prevent its contamination and to prevent it from contaminating other items.

Furthermore, it is preferred that the hub assembly 120 include a seal assembly 125 disposed at the first end 127 thereof. The seal assembly 125 preferably includes a resilient gasket type configuration and is structured to maintain the elongate tubular member 20 generally concentrically disposed through the hub assembly 120. Further, the seal assembly 125 is structured to engage the elongate tubular member 20 as it is withdrawn therethrough so as to substantially wipe off any accumulated secretions from its exterior surface and preferably provide a generally fluid impervious seal with the elongate tubular member 20 at the first end 127 of the hub assembly 120.

In addition to providing an effective connection point with the ventilator coupling 160, the hub assembly 120 is further structured and disposed to facilitate cleaning and irrigation of the second end 22 of the elongate tubular member 20 and the cleaning assembly 40', and can allow for testing of the cleaning assembly 40'. For example, the hub assembly 120 is preferably somewhat narrow at the first end 127, approximating a diameter of the endotracheal tube 80, and thereby helping to guide the elongate tubular member 20 along a concentric path and permitting a user to get a feel for the cleaning process while actually viewing the cleaning assembly 40' if a slight, cleaning type inflation of the resilient material bladder 40 is desired. Conversely, the hub assembly is generally wider at the second end 128 so as to permit full inflation of the resilient material bladder 40 if a test of its integrity or the loosening of built up secretion is necessary. In particular, the hub assembly 120 further includes a port 122 connected therewith. This port 122 may act as an irrigation port when cleaning of the second end 22 of the elongate tubular member 120 is desired. For example, as the elongate tubular member 20 is withdrawn from the endotracheal tube 80 after cleaning, the seal assembly 125 maintains all exterior excretions within the hub assembly. When the second end 22 of the elongate tubular member 20 is completely within the hub assembly 120, the hub assembly 120 is preferably removed from the ventilator coupling 160, and its second end 128 is preferably covered by a first cap section 130 of a sterile cap assembly, to be described in greater detail subsequently. Furthermore, the hub assembly 120 is preferably formed of a generally transparent material so as to permit viewing of the area to be cleaned. Once the hub assembly 120 is sealed, an irrigation fluid, preferably under some pressure is directed through the port 122 to wash off the second end 22 of the endotracheal tube 20, and therefore the cleaning assembly 40'. That irrigation fluid may then be drained or suctioned out.

Specifically, the port 122 is preferably coupled with a multi-port valve 144. As such, one auxiliary port 144' of the multi-port valve 144 may be connected via an appropriate suction coupling 148 to a suction hose 150, while another opening of the multi-port valve 144 is coupled in fluid flow communication with an irrigation fluid source, such as a syringe. Looking to the suction coupling 148, it may be covered with a corresponding cap 149 when not in use, however it will preferably be connected to a typical suction pump via a suction hose 150, a specimen trap 152 to filter out any suctioned particulate and collect them for analysis, and a secondary hose 154 connected to a suction source.

Furthermore, the suction means may also be coupled in fluid flow communication with the equilibrium channel 50. Specifically, the suction means when coupled with the equilibrium channel are structured and disposed to withdraw residue cleaned from the interior wall surface 83 of the endotracheal tube 80, and not captivated at or above the resilient material bladder 40 during cleansing. Moreover, the suction means can draw out watery secretions, which are generally more difficult to completely eliminate through the resilient material bladder 40 and expandable exterior sheath 42, through the equilibrium channel 50. Similarly, the suction means can function to suction a patients airway, beyond the endotracheal tube, in some circumstances, by introducing the second end 22 of the tubular member 20 beyond the endotracheal tube 80. With regard to the suction function, it is understood that the distal end port 52 of the equilibrium channel 50 may be disposed right at a tip of the second end 22 of the elongate tubular member 20, may be disposed in a side wall of the elongate tubular member 20, and/or may in fact include more than one port 52 so as to provide for more effective suction within the endotracheal tube 80. Further, it is also understood that the equilibrium channel 50 may be divided into a pair of channels, one to provide for suction and another to provide for alleviation of removal resisting suction pressure behind the resilient material bladder 40 during inflated removal.

Looking more particularly the preferred embodiment of the figures, the port 52 is preferably connected to an elongate, preferably flexible conduit 140 disposed at an intake port 195 of said handle assembly 190. Specifically, the intake port 195 of the handle assembly 190 is preferably connected in fluid flow communication with a port 54 of the equilibrium channel 50 disposed at the first end 24 of the elongate tubular member 20. This interconnection is preferably internal of the handle assembly 190 and may be accomplished by a molded interior channel or segment of flexible tubing 196. Of course, the intake port 195 of the handle assembly 190 may merely include an opening through which the conduit 140 extends for direct coupling with the port 54 of the equilibrium channel 50 or the interior channel 196. Moreover, the equilibrium channel 50 may extend to the intake port 195. In the preferred embodiment, however, a second multi-port valve 146 is coupled to the intake port 195, and the conduit 140 is coupled at opposite ends 141 and 142 thereof to the corresponding multi-port valves 144 and 146. In this configuration, it is seen that when the first multi-port valve 144 is positioned to direct flow between the suction coupling 148 and the conduit 140, and the second multi-port valve 146 is positioned to permit flow from the conduit 140 to the intake port 195, the suction is directed through the equilibrium channel 50 to achieve the airway suctioning function previously described. Moreover, use of these conventional multi-port valves 144 or 146 allows facilitated control of the application of suction merely by blocking or permitting flow. Conversely, during irrigation within the hub assembly 120, the first multi-port valve 144 may positioned to direct flow between the conduit 140 and the port 122, acting as the irrigation port, such that a syringe or other irrigation fluid source can be coupled with the conduit 140, such as at an auxiliary port 146' of the second multi-port valve 146 positioned to direct an irrigation fluid into the conduit 140, and can direct the fluid into the hub assembly 120. Subsequent to irrigation, the first multi-port valve 144 can be positioned to permit flow between the suction coupling 148 and the port 122 on the hub assembly 120 to suction out the irrigation fluid and any loosened debris. Alternatively, the irrigation fluid may be directed from a syringe through the second multi-port valve 146 directly into the equilibrium channel 50 for cleaning thereof. As such, irrigation fluid directed through either area will accumulate in the hub assembly 120 where the cleaning assembly 40', which must also be cleaned, is disposed.

The preferred embodiment of the present invention also includes a bypass coupling assembly. Specifically, the bypass coupling assembly is connected in fluid flow communication with the equilibrium channel 50 of the elongate tubular member 20, and the ventilator assembly 170. Moreover, the bypass coupling assembly is structured to automatically direct the air from the ventilator assembly 170 into the channel 50 of the elongate tubular member 20 and out the distal end of the channel 50 at the second end 52 of the elongate tubular member 20, upon occlusion of a flow of air through the endotracheal tube at a point of the endotracheal tube upstream of the distal end of the channel 50. Generally, this occlusion of air flow is a result of inflation of the resilient material bladder 40, and as such the distal end of the channel 50 located in a vicinity of the second end 22 of the elongate tubular member 20 is downstream of that point and is still in fluid flow communication with the patient. In the preferred embodiment, the bypass coupling assembly includes a bypass port disposed in fluid flow communication with a ventilator inlet port 165 of the ventilator coupling 160. As such, in the preferred embodiment, the port 122 of the hub assembly 120 acts as the bypass port. Moreover, the bypass coupling assembly includes the conduit 140 disposed in fluid flow communication between the bypass port 122 and the channel 50 of the elongate tubular member 20. Accordingly, if flow through the endotracheal tube 80 is constricted, the air flow backs up into the hub assembly 120 where it escapes through the bypass port 122. With proper positioning of the first and second multi-port valves 144 and 146, that ventilating air flows into the channel 50 and out to the patient. Along these lines it is noted, that the endotracheal tube cleaning apparatus 10 of the present invention may be easily adapted, merely by selectively actuating/positioning the first and the second multi-port valves 144 and 146, so as to selectively administer suction inside the endotracheal tube 80 through the channel 50, administer suction within the hub assembly 120 in order to withdraw secretions and irrigation fluid therefrom, administer medication in liquid form to the patient through the channel 50 at a point beyond the endotracheal tube 80 and well within the patient's airway, irrigate the cleaning assembly 40' within the hub assembly 120, irrigate the channel 50, preferably into the hub assembly 120, and ventilate the patient through the channel 50 by implementation of the bypass coupling. Accordingly, time consuming and potentially complex disconnection of the conduit 140 from its fluid flow communication between the bypass port 122 and the channel 50 of the elongate tubular member 20 can be eliminated, while still effectively performing a wide variety of functions.

In addition to the previously described preferred configuration of the endotracheal tube cleaning apparatus 10 of the present invention, the elongate tubular member 20 may include yet another elongate passage extending therethrough and having an outlet opening disposed generally at a point above the resilient material bladder 40. As such, during cleaning a suction can be applied above the resilient material bladder 40 to remove any loosened debris and/or fluid that may affect or hinder the cleaning process of the resilient material bladder 40. In this embodiment, the equilibrium channel 50 may be used to maintain respiratory air flow to the patient during cleaning as part of the bypass coupling assembly.

Yet another feature of the present invention, and preferably incorporated at the second multi-port valve 146, are medication administration means. Specifically, a standard MDI adaptor 180 type fixture can be coupled to the second multi-port valve 146 when it is positioned to direct flow between the adaptor 180 and the channel 50 through the intake port 195 of the handle assembly 190. As such, preferably upon removal of a protective cap 183, a medication vial 185 can be applied at the adaptor 180 and medication is administered into the channel 50. While the medication may flow directly down and out the distal end of the channel 50, generally the medication, especially liquid medication, will remain in the handle assembly 190 or upper region of the equilibrium channel 50 until the second multi-port valve 146 is positioned to block off the adaptor 180 and thereby open the conduit 140 permitting the bypass coupling assembly to be operational. At that point, the flow of air through the bypass coupling assembly functions to push the medication out the port 52 of the channel 50 disposed at the second end 22 of the elongate tubular member 20. As this can be accomplished when the elongate tubular member 20 is substantially introduced into the endotracheal tube 80, and therefore the patient, substantially direct and focused administration of the medication in the airway is ultimately achieved.

Referring once again to the sterile cap assembly of the present invention, it is seen to include a first cap section 130 and a second cap section 168. Specifically, the first cap section 130 of the sterile cap assembly is preferably structured to seal the second end 128 of the hub assembly 120 and thereby prevent an irrigating fluid from passing into the ventilator coupling 160 and subsequently into the endotracheal tube 80, as previously described. In particular, the first cap section 130 includes a sterile engagement face 132 that is matingly coupled with the second end 128 of the hub assembly 120. Moreover, it is preferred that the sterile engagement face 132 of the first cap section 130 be a male section structured to extend into the second end 128 of the hub assembly 120 to effectuate proper closure. Similarly, the second cap section 168 is preferably structured to be matingly coupled to the second inlet port 162 of the ventilator coupling 160, upon the hub assembly 120 and the ventilator coupling 160 being separated from one another. Significantly, however, it is preferred that the sterile engagement face 169 of the second cap section 168 be a female section structured to receive the second inlet port 162 of the ventilator coupling 160 therein. Of course, the male and female configurations can be varied to correspond to the necessary configurations of the hub assembly 120 and ventilator coupling 160, so long as they are opposite configurations. Specifically, in the preferred embodiment, the first and second cap sections 130 and 168 are each positionable between an open position and a closed position. In their respective closed positions, the corresponding sterile engagement faces 132 and 169 of the first and second cap sections 130 and 168 are correspondingly coupled in sealing relation at the second end 128 of the hub assembly 120 and at the second inlet port 162 of the ventilator coupling 160. When in the open position, however, due to the preferred opposing configurations of the sterile engagement faces 132 and 169, the sterile engagement faces 132 and 169 are structured to be selectively and matingly coupled with one another. Such coupling functions to maintain sterility of the sterile engagement faces 132 and 169 when not being used to cover the respective openings. Moreover, such interconnection generally stows the sterile cap assembly. It is seen that in a preferred embodiment, the first cap section 130 is tethered by an elongate segment to the hub assembly 120, preferably at an annular ridge 129 defined on the hub assembly 120, and the second cap section 168 is similarly tethered by an elongate segment to the ventilator coupling 160 at preferably an annular ridge defined on the ventilator coupling 160.

While this invention has been shown and described in what is considered to be a practical and preferred embodiment, it is recognized that departures may be made within the spirit and scope of this invention which should, therefore, not be limited except as set forth in the claims which follow and within the doctrine of equivalents. Furthermore, it is noted that the device of the present invention may also be utilized with similar medical tubes, such as a thoracostomy tube.

Now that the invention has been described,

What is claimed is:

1. An Endotracheal Tube Cleaning Apparatus to be used with an endotracheal tube having a distal end, a proximal end, and an interior wall structure defining a lumen therethrough; said endotracheal tube cleaning apparatus comprising:

an elongate tubular member, said elongate tubular member having a distal end structured to extend into the endotracheal tube, at least one channel defined in said elongate tubular member, said channel including a distal end disposed in a vicinity of said distal end of said elongate tubular member, a cleaning assembly disposed in said vicinity of said distal end of said elongate tubular member, said cleaning assembly being structured to engage the interior wall structure of the endotracheal tube for cleaning thereof, a ventilator coupling structured to be coupled to the endotracheal tube and including at least a first inlet port and a second inlet port, said first inlet port being coupled to a ventilator assembly structured to supply a fluid to a patient, said second inlet port being structured to receive said elongate tubular member therethrough into the endotracheal tube, and a bypass coupling assembly connected in fluid flow communication with said channel of said elongate tubular member and said ventilator assembly and structured to automatically direct the fluid from said ventilator assembly into the channel of the elongate tubular member and out said distal end of said channel of said elongate tubular member upon occlusion of a flow of the fluid through the endotracheal tube at a point of the endotracheal tube upstream of said distal end of said channel of said elongate tubular member.

2. An Endotracheal Tube Cleaning Apparatus as recited in claim 1 wherein said cleaning assembly is disposed along said elongate tubular member at a point proximal of said distal end of said channel, and is structured to engage the interior wall structure of the endotracheal tube and thereby occlude the flow of fluid through the endotracheal tube during cleaning.

3. An Endotracheal Tube Cleaning Apparatus as recited in claim 1 wherein said cleaning assembly comprises:

a resilient material bladder secured to said elongate tubular member and structured to inflate to a diameter sufficient to engage the interior wall surface of the endotracheal tube and occlude the flow of fluid through the endotracheal tube, and an inflation channel coupled in fluid flow communication with said resilient material bladder and structured to direct an inflation fluid into said resilient material bladder.

4. An Endotracheal Tube Cleaning Apparatus as recited in claim 3 wherein said inflation channel is defined in said elongate tubular member.

5. An Endotracheal Tube Cleaning Apparatus as recited in claim 3 wherein said resilient material bladder is disposed at a vicinity of said distal end of said elongate tubular member.

6. An Endotracheal Tube Cleaning Apparatus as recited in claim 3 wherein said cleaning assembly further includes an exterior abrasive surface disposed at least partially over said resilient material bladder and structured to engage the interior wall surface of the endotracheal tube, upon the resilient material bladder being inflated, and apply abrasive cleaning pressure to the interior wall surface of the endotracheal tube upon reciprocating movement of the elongate tubular member within the endotracheal tube.

7. An Endotracheal Tube Cleaning Apparatus as recited in claim 6 wherein said exterior abrasive surface is defined by an expandable exterior sheath structured to conform to said resilient material bladder upon inflation thereof, and to encase said resilient material bladder so as to contain said resilient material bladder in case of rupture.

8. An Endotracheal Tube Cleaning Apparatus as recited in claim 1 wherein said bypass coupling assembly comprises:

a bypass port disposed in fluid flow communication with said second inlet port of said ventilator coupling, and a conduit disposed in fluid flow communication between said bypass port and said channel of said elongate tubular member.

9. An Endotracheal Tube Cleaning Apparatus as recited in claim 8 further including a hub assembly structured to be coupled with said second inlet port of said ventilator coupling and receive said distal end of said elongate tubular member therethrough for subsequent passage into the endotracheal tube through said ventilator coupling.

10. An Endotracheal Tube Cleaning Apparatus as recited in claim 9 wherein said bypass port is disposed in said hub assembly.

11. An Endotracheal Tube Cleaning Apparatus as recited in claim 10 further including a first multi-port valve disposed in fluid flow communication between said conduit and said bypass port and including an auxiliary port, and a second multi-port valve disposed in fluid flow communication between said conduit and said channel and including an auxiliary port, said auxiliary ports of said first and said second multi-port valves being selectively coupled with a medication administration adaptor, an irrigation fluid source, and a suction source, and said first and said second multi-port valves being structured to be selectively actuated so as to selectively administer suction inside the endotracheal tube through said channel, administer suction within said hub assembly to withdraw secretions and irrigation fluid, administer medication to the patient through said channel at a point beyond the endotracheal tube, irrigate said cleaning assembly within said hub assembly, irrigate said channel, and ventilate the patient through said channel, without disconnection of said conduit from said fluid flow communication between said bypass port and said channel of said elongate tubular member.

12. An Endotracheal Tube Cleaning Apparatus as recited in claim 1 further including a hub assembly having a first end and a second end, said second end being structured to be coupled with said second inlet port of said ventilator coupling and receive said distal end of said elongate tubular member therethrough for subsequent passage into the endotracheal tube through said ventilator coupling.

13. An Endotracheal Tube Cleaning Apparatus as recited in claim 12 wherein said hub assembly further includes a seal assembly disposed at said first end of said hub assembly, said seal assembly being structured to maintain said elongate tubular member generally concentrically disposed through said hub assembly, and to engage said elongate tubular member as it is withdrawn therethrough so as to substantially wipe off said elongate tubular member and provide a generally fluid impervious seal with said elongate tubular member at said first end of said hub assembly.

14. An Endotracheal Tube Cleaning Apparatus as recited in claim 12 further including an irrigation port disposed in said hub assembly and structured to provide for direct cleaning and irrigation of said distal end of said elongate tubular member and said cleaning assembly.

15. An Endotracheal Tube Cleaning Apparatus as recited in claim 14 further including a sterile cap assembly structured to seal said second end of said hub assembly and thereby prevent an irrigating fluid from passing into said ventilator coupling and subsequently into the endotracheal tube.

16. An Endotracheal Tube Cleaning Apparatus as recited in claim 15 wherein said sterile cap assembly includes a first cap section and a second cap section, said first cap section being structured to be matingly coupled to said second end of said hub assembly and said second cap section being structured to be matingly coupled to said second inlet port of said ventilator coupling, upon said hub assembly and said ventilator coupling being separated from one another.

17. An Endotracheal Tube Cleaning Apparatus as recited in claim 16 wherein said first cap section and said second cap section of said sterile cap assembly each include a sterile engagement face structured to be correspondingly exposed to an interior of said hub assembly and an interior of said ventilator coupling, said sterile engagement face of said first cap section being structured to be selectively and matingly coupled with said sterile engagement face of said second cap section, upon said hub assembly being coupled to said ventilator coupling, so as to maintain sterility of said sterile engagement faces.

18. An Endotracheal Tube Cleaning Apparatus as recited in claim 17 wherein said first cap section is structured to be secured to said hub assembly so as to be positionable between an open position wherein said sterile engagement face of said first cap section is coupled to said sterile engagement face of said second cap section, and a closed position wherein said sterile engagement face of said first cap section is matingly coupled to said second end of said hub assembly so as to seal said second end of said hub assembly.

19. An Endotracheal Tube Cleaning Apparatus as recited in claim 17 wherein said second cap section is structured to be secured to said ventilator coupling so as to be positionable between an open position wherein said sterile engagement face of said second cap section is coupled to said sterile engagement face of said first cap section, and a closed position wherein said sterile engagement face of said second cap section is matingly coupled to said second inlet port of said ventilator coupling so as to seal said second inlet port of said ventilator coupling.

20. An Endotracheal Tube Cleaning Apparatus as recited in claim 1 further including suction means coupled in fluid flow communication with said channel of said elongate tubular member and structured and disposed to apply a suction force therethrough.

21. An Endotracheal Tube Cleaning Apparatus as recited in claim 1 further including medication administration means coupled in fluid flow communication with said channel of said elongate tubular member and structured and disposed to provide for a supply of a quantity of medication therethrough and into said channel for subsequent administration to the patient.

22. An Endotracheal Tube Cleaning Apparatus to be used with an endotracheal tube having a distal end, a proximal end, and an interior wall structure defining a lumen therethrough; said endotracheal tube cleaning apparatus comprising:

an elongate tubular member, said elongate tubular member having a distal end structured to extend into the endotracheal tube, a cleaning assembly disposed in a vicinity of said distal end of said elongate tubular member, said cleaning assembly being structured to engage the interior wall structure of the endotracheal tube for cleaning thereof, a ventilator coupling structured to be coupled to the endotracheal tube and including at least one inlet port structured to receive said elongate tubular member therethrough into the endotracheal tube, a hub assembly structured to be coupled with said inlet port of said ventilator coupling and receive said distal end of said elongate tubular member therethrough for subsequent passage into the endotracheal tube through said ventilator coupling, and an irrigation port disposed in said hub assembly and structured to provide for direct cleaning and irrigation of said distal end of said elongate tubular member and said cleaning assembly.

23. An Endotracheal Tube Cleaning Apparatus as recited in claim 22 wherein said hub assembly further includes a seal assembly disposed at a first end thereof, said seal assembly being structured to maintain said elongate tubular member generally concentrically disposed through said hub assembly, and to engage said elongate tubular member as it is withdrawn therethrough so as to substantially wipe off said elongate tubular member and provide a generally fluid impervious seal with said elongate tubular member at said first end of said hub assembly.

24. An Endotracheal Tube Cleaning Apparatus as recited in claim 22 further including a sterile cap assembly structured to seal a second end of said hub assembly and thereby prevent an irrigating fluid from passing into said ventilator coupling and subsequently into the endotracheal tube.

25. An Endotracheal Tube Cleaning Apparatus as recited in claim 24 wherein said sterile cap assembly includes a first cap section and a second cap section, said first cap section being structured to be matingly coupled to said second end of said hub assembly and said second cap section being structured to be matingly coupled to said inlet port of said ventilator coupling, upon said hub assembly and said ventilator coupling being separated from one another.

26. An Endotracheal Tube Cleaning Apparatus as recited in claim 25 wherein said first cap section and said second cap section of said sterile cap assembly each include a sterile engagement face structured to be correspondingly exposed to an interior of said hub assembly and an interior of said ventilator coupling, said sterile engagement face of said first cap section being structured to be selectively and matingly coupled with said sterile engagement face of said second cap section, upon said hub assembly being coupled to said ventilator coupling, so as to maintain sterility of said sterile engagement faces.

27. An Endotracheal Tube Cleaning Apparatus as recited in claim 26 wherein said first cap section is structured to be secured to said hub assembly so as to be positionable between an open position wherein said sterile engagement face of said first cap section is coupled to said sterile engagement face of said second cap section, and a closed position wherein said sterile engagement face of said first cap section is matingly coupled to said second end of said hub assembly so as to seal said second end of said hub assembly.

28. An Endotracheal Tube Cleaning Apparatus as recited in claim 26 wherein said second cap section is structured to be secured to said ventilator coupling so as to be positionable between an open position wherein said sterile engagement face of said second cap section is coupled to said sterile engagement face of said first cap section, and a closed position wherein said sterile engagement face of said second cap section is matingly coupled to said inlet port of said ventilator coupling so as to seal said inlet port of said ventilator coupling.

29. An Endotracheal Tube Cleaning Apparatus as recited in claim 22 wherein said cleaning assembly comprises:

a resilient material bladder secured to said elongate tubular member and structured to inflate to a diameter sufficient to engage the interior wall surface of the endotracheal tube, and an inflation channel coupled in fluid flow communication with said resilient material bladder and structured to direct an inflation fluid into said resilient material bladder.

30. An Endotracheal Tube Cleaning Apparatus as recited in claim 29 wherein said inflation channel is defined in said elongate tubular member.

31. An Endotracheal Tube Cleaning Apparatus as recited in claim 29 wherein said cleaning assembly further includes an exterior abrasive surface disposed at least partially over said resilient material bladder and structured to engage the interior wall surface of the endotracheal tube, upon the resilient material bladder being inflated, and apply abrasive cleaning pressure to the interior wall surface of the endotracheal tube upon reciprocating movement of the elongate tubular member within the endotracheal tube.

32. An Endotracheal Tube Cleaning Apparatus as recited in claim 31 wherein said exterior abrasive surface is defined by an expandable exterior sheath structured to conform to said resilient material bladder upon inflation thereof, and to encase said resilient material bladder so as to contain said resilient material bladder in case of rupture.

33. An Endotracheal Tube Cleaning Apparatus as recited in claim 22 wherein said elongate tubular member further includes a channel defined therein, a distal end of said channel being disposed in a vicinity of said distal end of said elongate tubular member.

34. An Endotracheal Tube Cleaning Apparatus as recited in claim 33 further including a bypass coupling assembly connected in fluid flow communication with said channel of said elongate tubular member and a ventilator assembly and structured to automatically direct fluid from said ventilator assembly into said channel of the elongate tubular member and out said distal end of said channel of said elongate tubular member upon occlusion of a flow of the fluid through the endotracheal tube at a point of the endotracheal tube upstream of said distal end of said channel of said elongate tubular member.

35. An Endotracheal Tube Cleaning Apparatus as recited in claim 34 wherein said irrigation port is further structured to define a bypass port of said bypass coupling assembly.

36. An Endotracheal Tube Cleaning Apparatus as recited in claim 33 further including suction means coupled in fluid flow communication with said channel of said elongate tubular member and structured and disposed to apply a suction force therethrough.

37. An Endotracheal Tube Cleaning Apparatus as recited in claim 33 further including medication administration means coupled in fluid flow communication with said channel of said elongate tubular member and structured and disposed to provide for a supply of a quantity of medication therethrough and into said channel for subsequent administration to a patient.

38. An Endotracheal Tube Cleaning Apparatus as recited in claim 22 wherein said hub assembly is formed of a substantially transparent material so as to permit viewing of said distal end of said elongate tubular member during cleaning.

39. An Endotracheal Tube Cleaning Apparatus as recited in claim 22 wherein said hub assembly includes a generally narrow diameter first end structured to guide concentric passage of said elongate tubular member into the endotracheal tube through said ventilator coupling.

* * * * *